United States Patent
Krupka et al.

[11] Patent Number: 6,132,337
[45] Date of Patent: Oct. 17, 2000

[54] EXERCISE MONITORING SYSTEM

[75] Inventors: Yaakov Krupka; Eyal Krupka, both of Rehovot; Eli Zilka, Petach Tikva, all of Israel

[73] Assignee: Keytron Electronics & Technologies Ltd., Rehovot, Israel

[21] Appl. No.: 09/047,105

[22] Filed: Mar. 24, 1998

[30] Foreign Application Priority Data

Mar. 24, 1997 [IL] Israel ........................................ 120507

[51] Int. Cl.$^7$ ........................................ A61B 5/04
[52] U.S. Cl. ........................ 482/8; 482/1; 482/9; 482/900
[58] Field of Search ........................... 482/1–9, 900–902

[56] References Cited

U.S. PATENT DOCUMENTS

| | | |
|---|---|---|
| 3,709,042 | 1/1973 | Lee et al. . |
| 3,797,010 | 3/1974 | Adler et al. . |
| 4,140,132 | 2/1979 | Dahl ......................................... 607/19 |
| 4,202,350 | 5/1980 | Walton .................................... 600/503 |
| 4,230,127 | 10/1980 | Larson .................................... 600/519 |
| 4,295,472 | 10/1981 | Adams .................................... 600/503 |
| 4,307,727 | 12/1981 | Haynes .................................... 600/485 |
| 4,331,154 | 5/1982 | Broadwater et al. .................... 600/490 |
| 4,409,983 | 10/1983 | Albert ...................................... 600/503 |
| 4,425,921 | 1/1984 | Fujisaki et al. .......................... 600/503 |
| 4,428,378 | 1/1984 | Anderson et al. ........................ 607/19 |
| 4,434,801 | 3/1984 | Jiminez et al. .......................... 600/502 |
| 4,489,731 | 12/1984 | Baumberg ................................ 600/503 |
| 4,765,323 | 8/1988 | Poettgen ................................... 128/849 |
| 4,807,639 | 2/1989 | Shimizu et al. .......................... 600/503 |
| 4,907,795 | 3/1990 | Shaw et al. . |
| 4,926,863 | 5/1990 | Alt ............................................ 607/19 |
| 4,938,228 | 7/1990 | Righter et al. ........................... 600/503 |
| 5,014,700 | 5/1991 | Alt ............................................ 607/19 |
| 5,031,615 | 7/1991 | Alt ............................................ 607/19 |
| 5,179,947 | 1/1993 | Meyerson et al. ....................... 607/19 |
| 5,197,489 | 3/1993 | Conlan .................................... 600/595 |
| 5,228,449 | 7/1993 | Christ et al. ............................. 600/504 |
| 5,314,389 | 5/1994 | Dotan ....................................... 482/3 |
| 5,316,008 | 5/1994 | Suga et al. ............................... 600/513 |
| 5,330,510 | 7/1994 | Legay et al. ............................. 607/19 |
| 5,342,404 | 8/1994 | Alt et al. ..................................... 607/6 |
| 5,354,317 | 10/1994 | Alt ............................................ 607/19 |
| 5,370,667 | 12/1994 | Alt ............................................ 607/19 |
| 5,382,473 | 1/1995 | Musclow et al. ........................ 428/353 |
| 5,383,826 | 1/1995 | Michael ...................................... 482/3 |
| 5,394,879 | 3/1995 | Gorman ................................... 600/520 |
| 5,403,256 | 4/1995 | Squires ...................................... 482/91 |
| 5,423,869 | 6/1995 | Poore et al. .............................. 607/18 |
| 5,425,750 | 6/1995 | Moberg .................................... 607/19 |
| 5,462,504 | 10/1995 | Trulaske et al. ........................... 482/7 |
| 5,464,021 | 11/1995 | Birnbaum ................................ 600/509 |
| 5,466,200 | 11/1995 | Ulrich et al. . |
| 5,467,771 | 11/1995 | Narimatsu et al. ...................... 600/485 |
| 5,474,077 | 12/1995 | Suga ........................................ 600/500 |
| 5,486,818 | 1/1996 | Loponen .............................. 340/870.31 |
| 5,497,779 | 3/1996 | Takaya et al. ........................... 600/485 |
| 5,527,239 | 6/1996 | Abbondanza ............................... 482/8 |
| 5,547,439 | 8/1996 | Rawls et al. . |
| 5,577,981 | 11/1996 | Jarvik . |
| 5,591,104 | 1/1997 | Andrus et al. . |
| 5,598,849 | 2/1997 | Browne . |
| 5,702,323 | 12/1997 | Poulton ....................................... 482/9 |

OTHER PUBLICATIONS

Edward L. Melanson, Jr. and Patty S. Freedson, "Medicine and Science in Sports and Exercise," Validity of the Computer Science and Applications, Inc. (CSA) Activity Monitor, 1995, pp. 934–940.

*Primary Examiner*—Glenn E. Richman
*Attorney, Agent, or Firm*—Mark M. Friedman

[57] ABSTRACT

This invention discloses an interactive exercise monitoring system including a body mounted motion sensor, and a user sensible output indicator indicating to a user an exercise motion parameter derived from an output of the body mounted motion sensor as well as a desired exercise motion parameter for comparison therewith.

A method for interactive exercise monitoring is also disclosed.

5 Claims, 11 Drawing Sheets

Microfiche Appendix Included
(1 Microfiche, 98 Pages)

EXERCISE MONITORING SYSTEM

REFERENCE TO RELATED APPLICATIONS

This application claims priority to Israeli patent application number 120507 filed on Mar. 24, 1997.

MICROFICHE APPENDIX

This application contains Microfiche Appendix A consisting of two (2) slides and 184 frames.

FIELD OF THE INVENTION

The present invention relates to exercise monitoring systems generally.

BACKGROUND OF THE INVENTION

Various types of exercise monitoring systems are known in the prior art patent literature.

U.S. Pat. No. 5,527,239 describes a pulse rate controlled exercise system which includes a pulse rate monitor and a user viewable display which indicates the user's pulse rate during exercise.

U.S. Pat. No. 5,598,849 describes an interactive exercise monitoring system and method which also includes a pulse rate monitor and which is interconnected via a modem with a network for downloading exercise regime data to guide a user.

U.S. Pat. No. 5,466,200 describes interactive exercise apparatus which displays a user's progress through a simulated environment.

U.S. Pat. No. 5,547,439 describes an exercise system using a plurality of exercise cycles and a display indicating progress of multiple cycles along a simulated travel path.

U.S. Pat. No. 4,907,795 describes a computerized exercise monitoring system and method for monitoring a user's exercise performance, wherein current performance is compared with a user's past performance.

U.S. Pat. No. 5,591,104 describes a physical exercise video system including an interface between an exercise machine and a video monitor.

U.S. Pat. No. 5,577,981 describes a virtual reality exercise machine and computer controlled video system.

U.S. Pat. No. 5,383,826 describes a user interface console for exercise equipment including a display for displaying various exercise parameters.

U.S. Pat. No. 5,403,256 describes aerobic apparatus for providing support and coordination of exercise motions to a user.

Various types of body mounted exercise devices employing accelerometers are described in the following U.S. Patents: Nos. 3,797,010; 4,7765,323; 5,330,510; 4,428,378; 4,926,863; 5,354,317; 5,425,750; 5,031,615; 5,382,473; 5,342,404; 5,179,947; 5,423,869; 4,140,132; 5,014,700; 5,370,667.

Various types of heart monitors are described in the following U.S. Patents: Nos. 5,497,779; 5,474,077; 5,467,771; 5,464,021; 5,316,008; 5,228,449; 5,197,489; 4,938,228; 4,807,639; 4,489,731; 4,425,921; 4,409,983; 4,331,154; 4,307,727; 4,295,472; 4,230,127; 4,202,350.

Additional U.S. Patents of interest include: Nos. 3,709,042; 4,434,801; 5,314,389; 5,394,879; 5,486,818.

Attention is also directed to Validity of the Computer Science and Applications, Inc. (CSA) activity monitor by Edward L. Melanson, Jr. and Patty S. Freedson, Medicine and Science in Sports and Exercise, 1995, pp 934–940.

SUMMARY OF THE INVENTION

The present invention seeks to provide an interactive exercise monitoring system which may be independent of an exercise machine.

There is thus provided in accordance with a preferred embodiment of the present invention an interactive exercise monitoring system including:

a body mounted motion sensor; and a user sensible output indicator indicating to the user an exercise motion parameter derived from an output of the body mounted motion sensor as well as a desired exercise motion parameter for comparison therewith.

There is also provided in accordance with a preferred embodiment of the present invention an interactive exercise monitoring system including:

a body mounted heart rate sensor; and a user sensible output indicator indicating to the user a desired exercise motion parameter derived from a comparison of a desired range of heart rate parameters with the direction of change and rate of change of the user's heart rate as determined by the sensor.

In accordance with a preferred embodiment of the present invention, the interactive exercise monitoring system is a combination of all of the foregoing elements.

There is additionally provided in accordance with a preferred embodiment of the present invention an interactive exercise monitoring method including:

using a body mounted motion sensor to sense user motion during exercise; and indicating to the user an exercise motion parameter derived from an output of the body mounted motion sensor as well as a desired exercise motion parameter for comparison therewith.

There is further provided in accordance with a preferred embodiment of the present invention an interactive exercise monitoring method including:

sensing the user's heart rate; and indicating to the user a desired exercise motion parameter derived from a comparison of a desired range of heart rate parameters with the direction of change and rate of change of the user's heart rate.

In accordance with a preferred embodiment of the present invention, the interactive exercise monitoring method is a combination of all of the foregoing steps.

In accordance with a preferred embodiment of the invention the user sensible output indicator and the indicating step employ both visual and audible indications. Alternatively either may be employed. Preferably, the visual indicator indicates the motion that the user is supposed to carry out and the audible indicator indicates the tempo at which the motion is to be carried out.

In accordance with a preferred embodiment of the present invention, the method and system sense whether the user is about to exceed desired upper or lower limits of heart rate and prophylactically changes the tempo, prior to exceedence of such limits, so as to urge the user to stay within the limits.

Further in accordance with a preferred embodiment of the present invention, a visual indicator indicates on a time scale both a desired pattern of movements and the user's actual pattern of movements, so as to enable and encourage the user to bring his movements into phase and tempo with the desired pattern.

In accordance with a preferred embodiment of the present invention, the body mounted heart rate sensor and motion sensor are both incorporated in a single belt worn by the user during exercise. Preferably, the belt communicates via a wireless link with the indicator apparatus.

BRIEF DESCRIPTION OF THE DRAWINGS

The present invention will be understood and appreciated more fully from the following detailed description, taken in conjunction with the drawings in which.

LIST OF APPENDICES

Appendix A is a hexadecimal listing of the object code of a preferred embodiment of control program 62 and of exercise program 64; loading instructions are described hereinbelow.

DETAILED DESCRIPTION OF A PREFERRED EMBODIMENT

Figure 1:
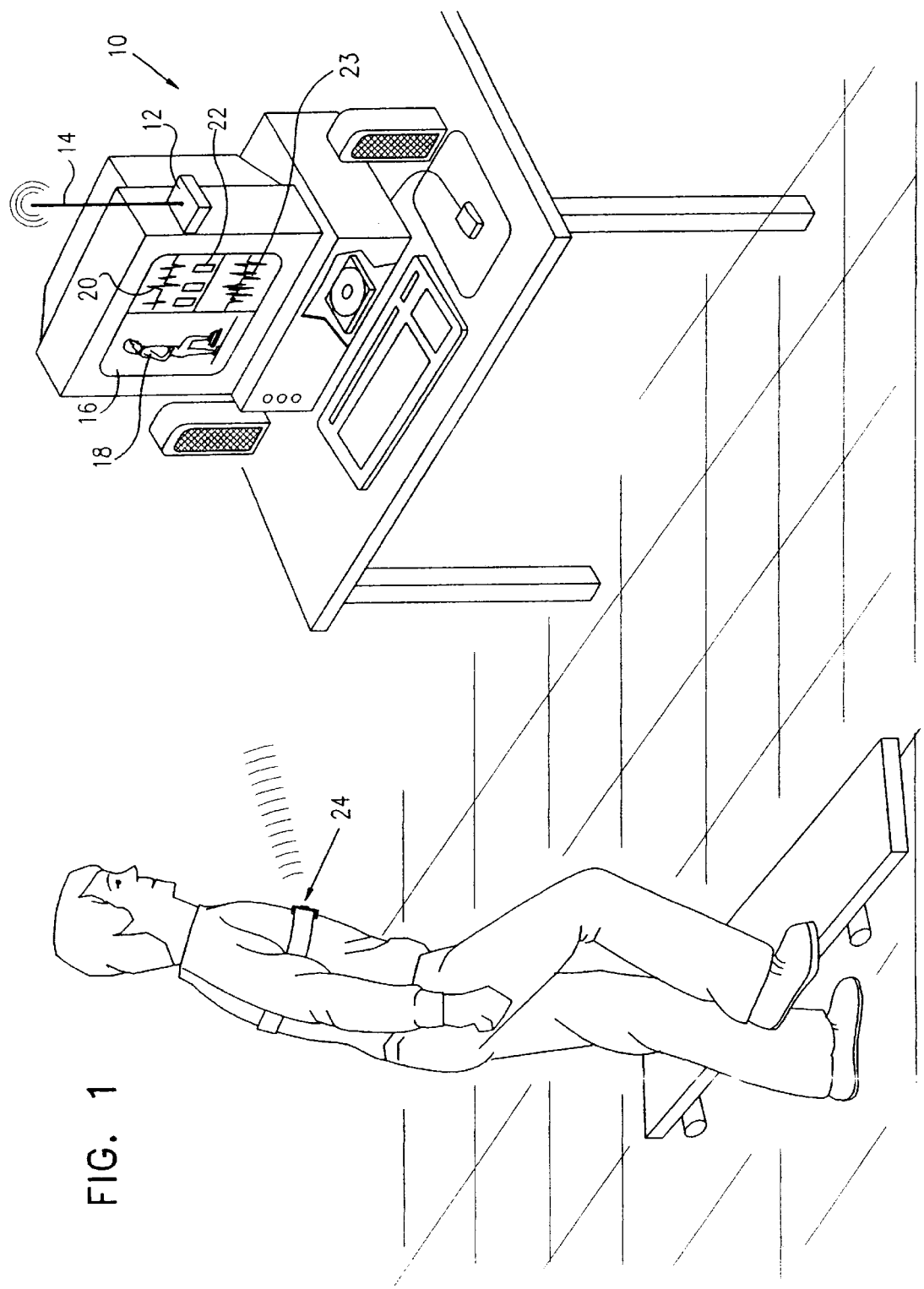
FIG. 1 is a simplified pictorial illustration of an exercise monitor system constructed and operative in accordance with a preferred embodiment of the present invention.

Reference is now made to FIG. 1, which illustrates an exercise monitor system constructed and operative in accordance with a preferred embodiment of the present invention. The system preferably comprises a conventional personal computer 10, such as an IBM or IBM compatible 486 with a disk or CD ROM drive and an audio card and enhanced audio apparatus. Associated with the computer 10 is preferably an RF receiver assembly 12 including an antenna 14.

In accordance with a preferred embodiment of the present invention, a display screen 16 of the computer 10 displays a number of exercise parameters, preferably including an animated image 18 illustrating an exercise to be carried out, a time graph 20 indicating a pattern and timing of desired motion corresponding to the exercise illustrated by animated image 18, one or more additional exercise parameter indicators 22, including, for example, user heart rate, desired heart rate, calories expended, time elapsed, etc.

It is a particular feature of the present invention, that the display screen 16 also preferably indicates in real time the pattern and timing 23 of the actual motion of the user in real time. This display enables a user to match his activity, in terms of motion and the timing thereof to the desired motion pattern and its timing.

The user parameters, such as heart rate and motion are communicated to the computer 10 via receiver assembly 12 by a body mounted transducer assembly 24, typically in the form of a chest belt worn by the user either under or over his clothing. If the electrodes do not directly contact the body of the user, the intervening clothing at the electrode locations should be dampened so as to be electrically conductive.

Figure 2:
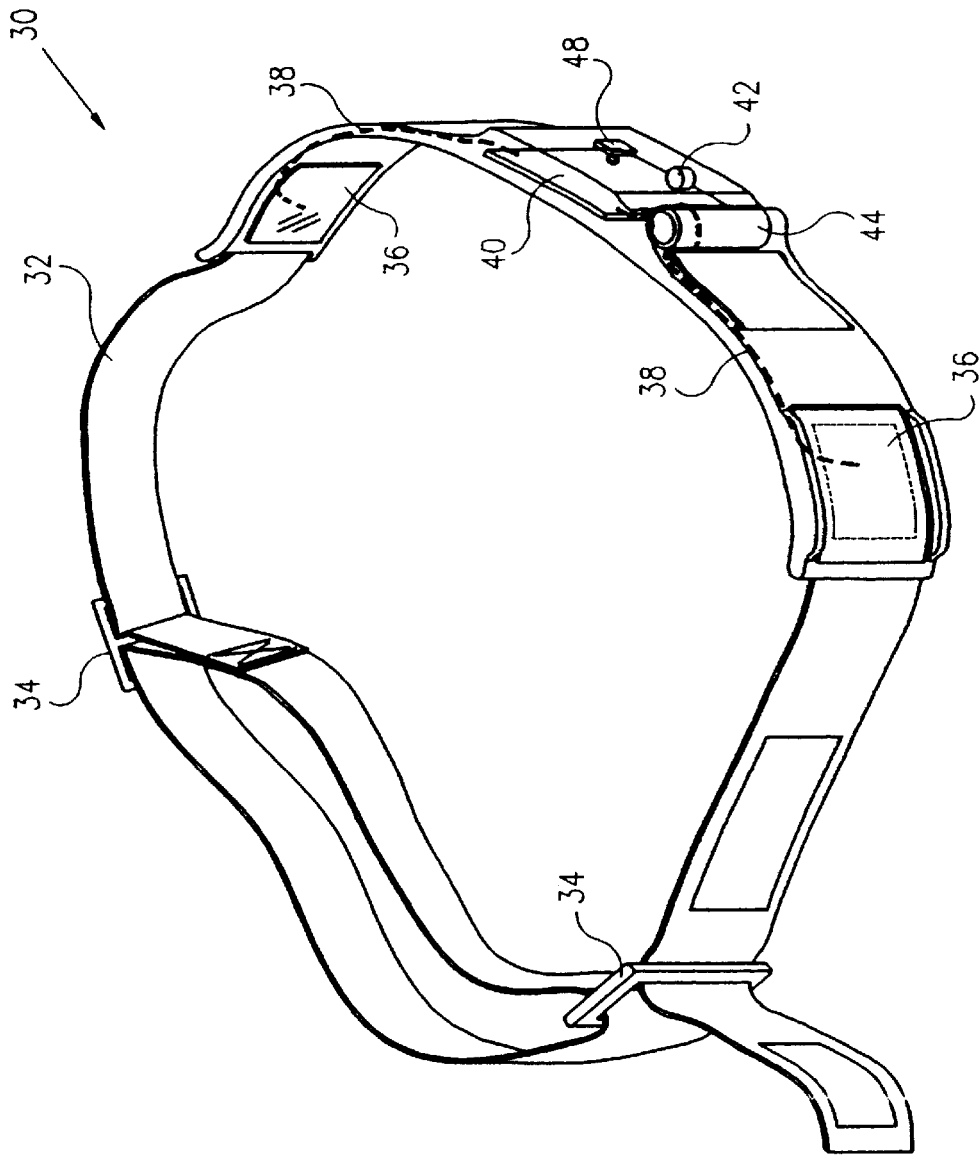
FIG. 2 is a simplified pictorial illustration of a body mountable sensor belt useful in the system of FIG. 1.

Reference is now made to FIG. 2, which is a simplified pictorial illustration of a body mountable sensor belt useful in the system of FIG. 1. The belt, indicated generally by reference numeral 30, comprises a strap 32, typically of an elastic substrate, with associated buckles 34 for adjustment. Mounted on strap 30 and facing inwardly are at least two heart rate sensor (ECG) electrodes 36 which are coupled by suitable conductors 38 to signal processing circuitry 40. Signal processing circuitry 40 also receives an input from an accelerometer 42, such as an MTC-1 accelerometer commercially available from Hephzibah Industries Co. of Inchon, Korea, and power from batteries 44 and provides a wireless output via an antenna which is preferably embodied in conductor 38. An ON-OFF/ADVANCE switch 48 enables the user to selectably activate the circuitry of belt 30 and control operation of additional features of the system.

Figure 3:
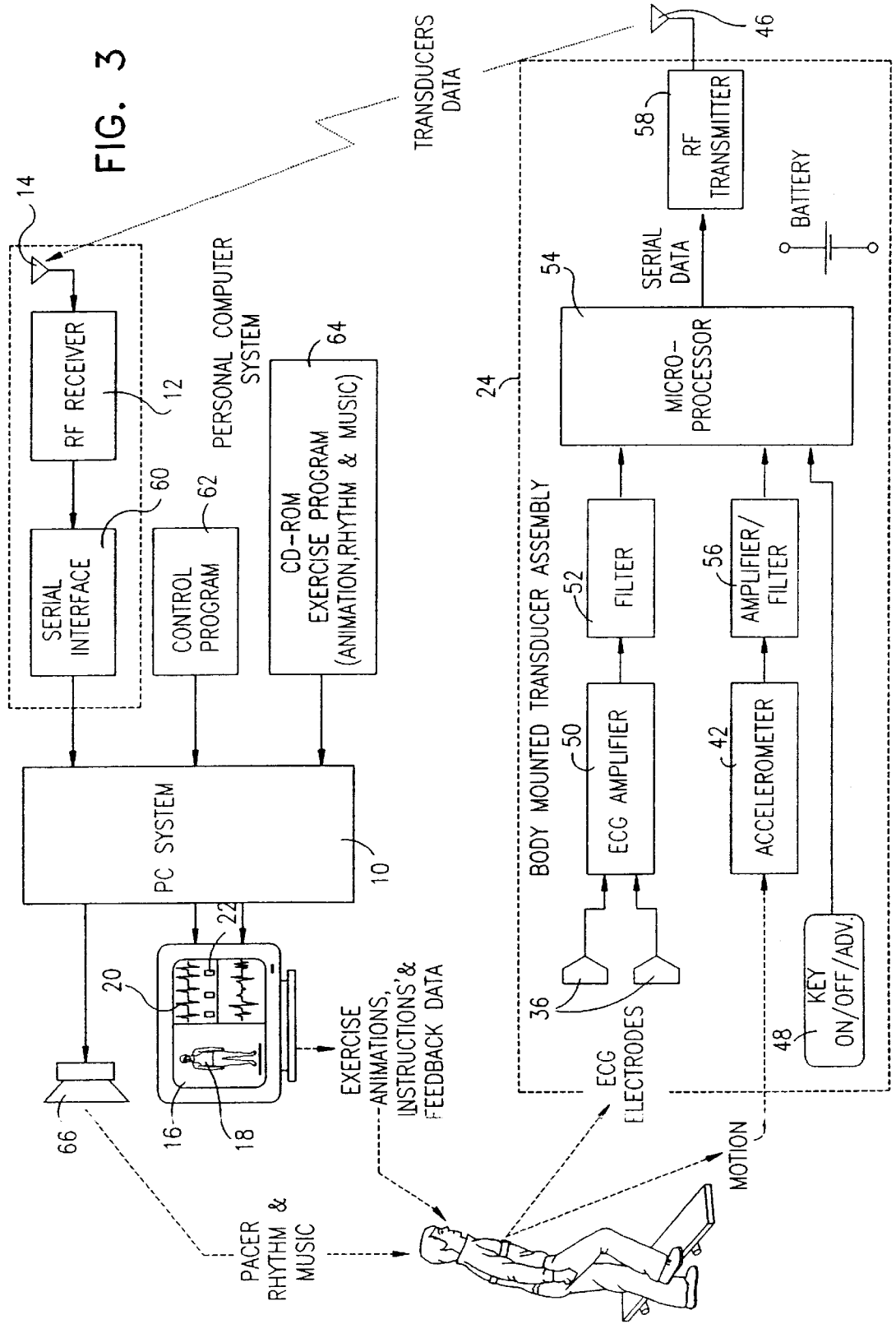
FIG. 3 is a simplified block diagram illustration of the system of FIG. 1.

Reference is now made to FIG. 3, which is a simplified block diagram illustration of the system of FIG. 1. It is seen that in the body mounted transducer assembly 24, ECG electrodes 36 output to an ECG amplifier 50, which in turn, outputs via a filter 52 to a microprocessor 54. Accelerometer 42 preferably outputs via an amplifier/filter assembly 56 to microprocessor 54.

Microprocessor 54 preferably outputs serial data via an RF transmitter 58 and antenna 46 to wireless receiver assembly 12 via antenna 14. Receiver assembly 12 preferably outputs via a serial interface 60 to the computer 10, which receives inputs from a control program 62 and an application program 64, which is typically embodied in a CD-ROM and includes at least animation, rhythm, and music inputs. An example of a preferred embodiment of control program 62 and application program 64 is set forth in Appendix A.

Display screen 16 receives inputs representing both desired exercise parameters and real time user exercise parameters, also referred to as feedback data, from the computer 10 and displays them for the user. A speaker 66 preferably provides a pacer rhythm and music which is time coordinated with the images displayed to the user.

Figure 4:
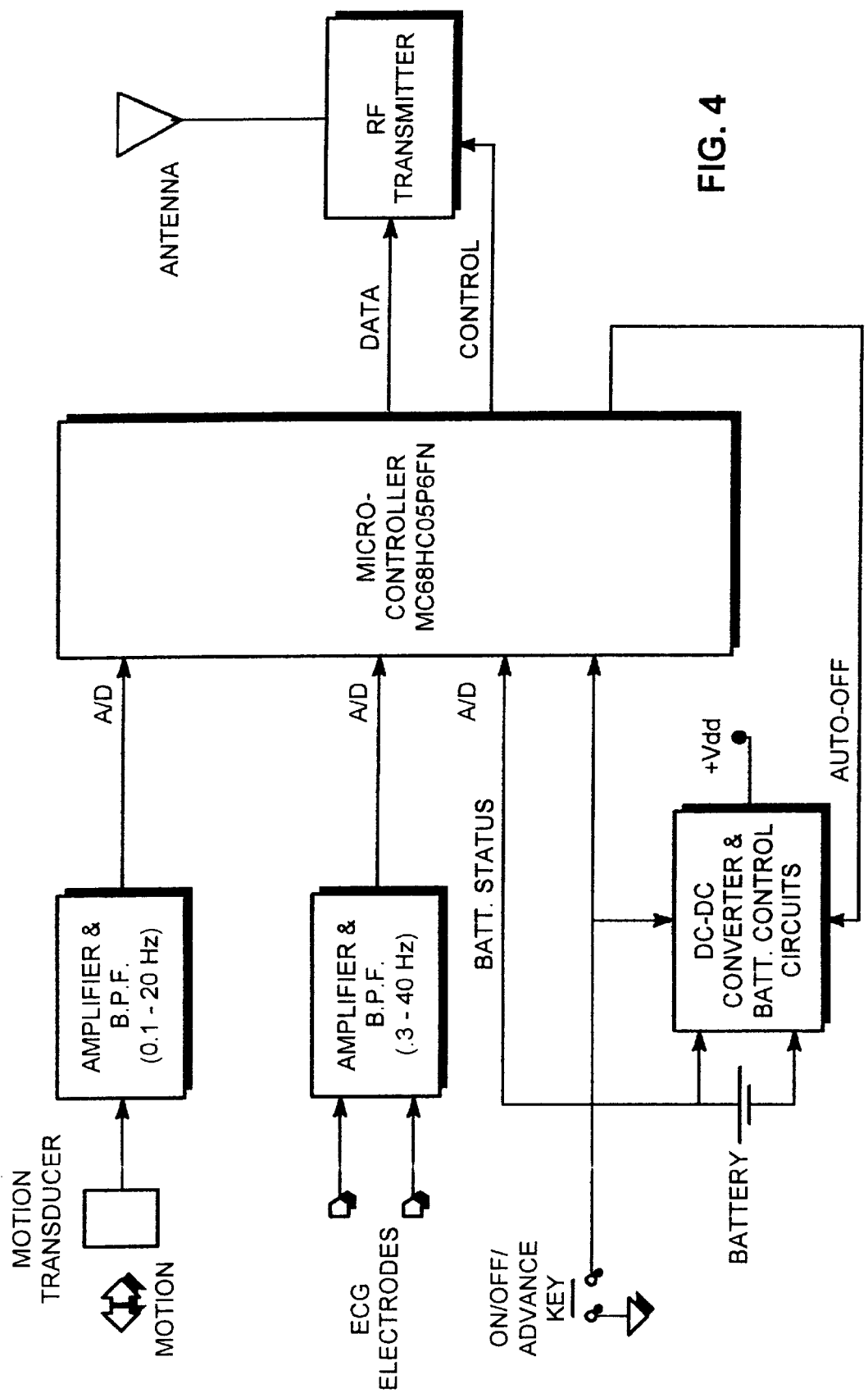
FIG. 4 is a simplified block diagram illustration of the electronic circuitry employed in the belt of FIG. 2.
Figure 5A:
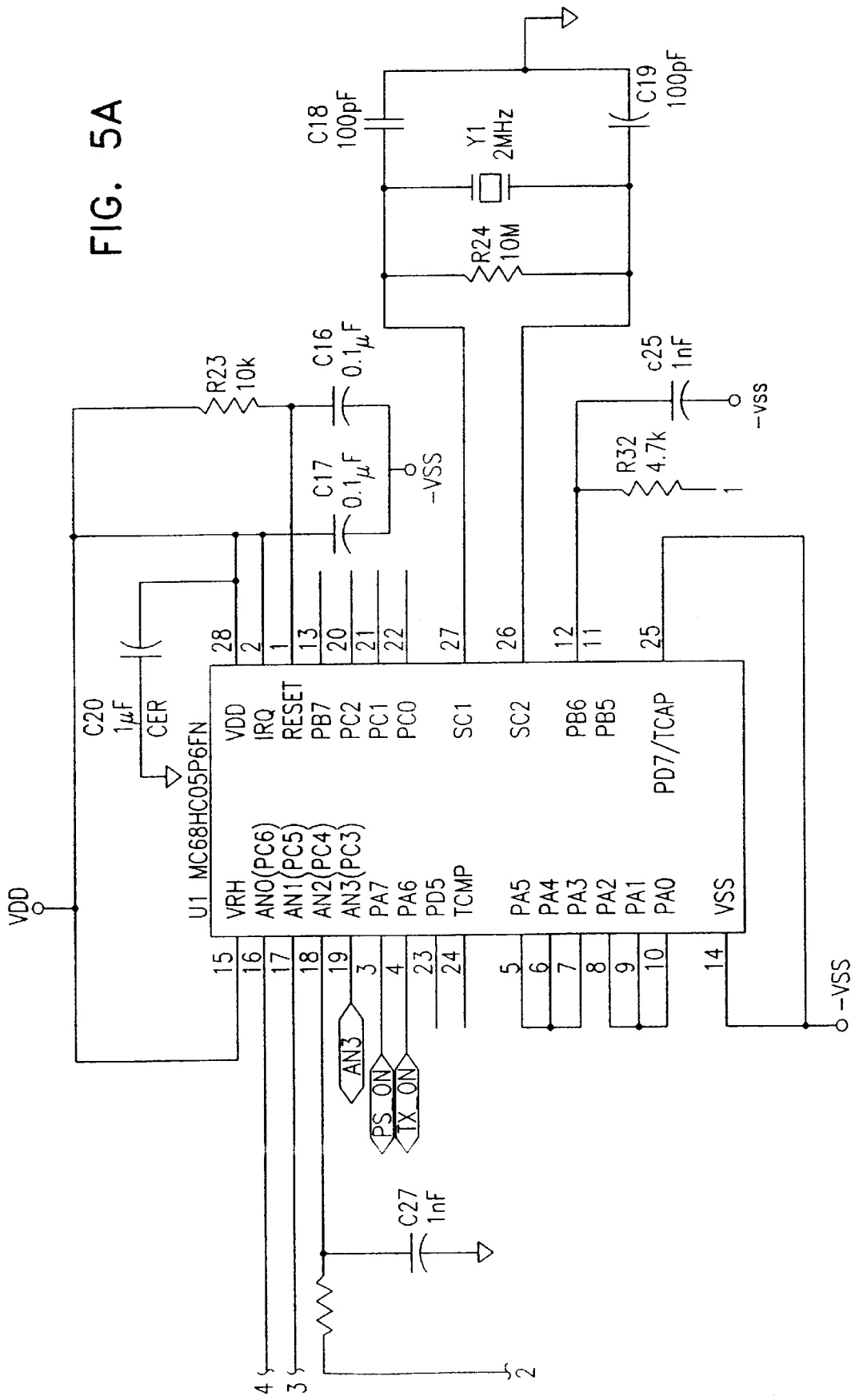
FIGS. 5A, 5B, 5C and 5D are together a schematic illustration of the electronic circuitry of FIG. 4.
Figure 5B:
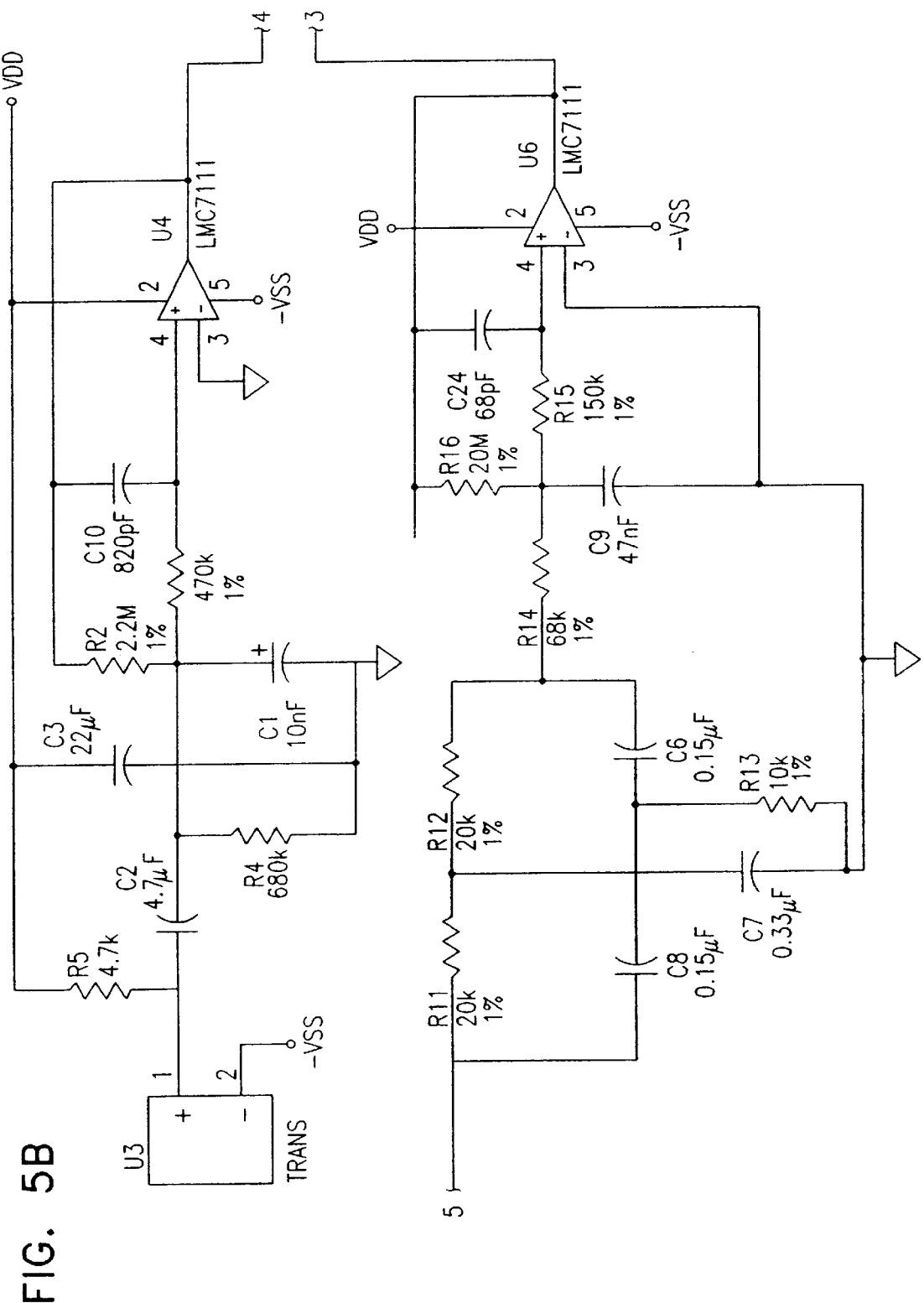
Figure 5C:
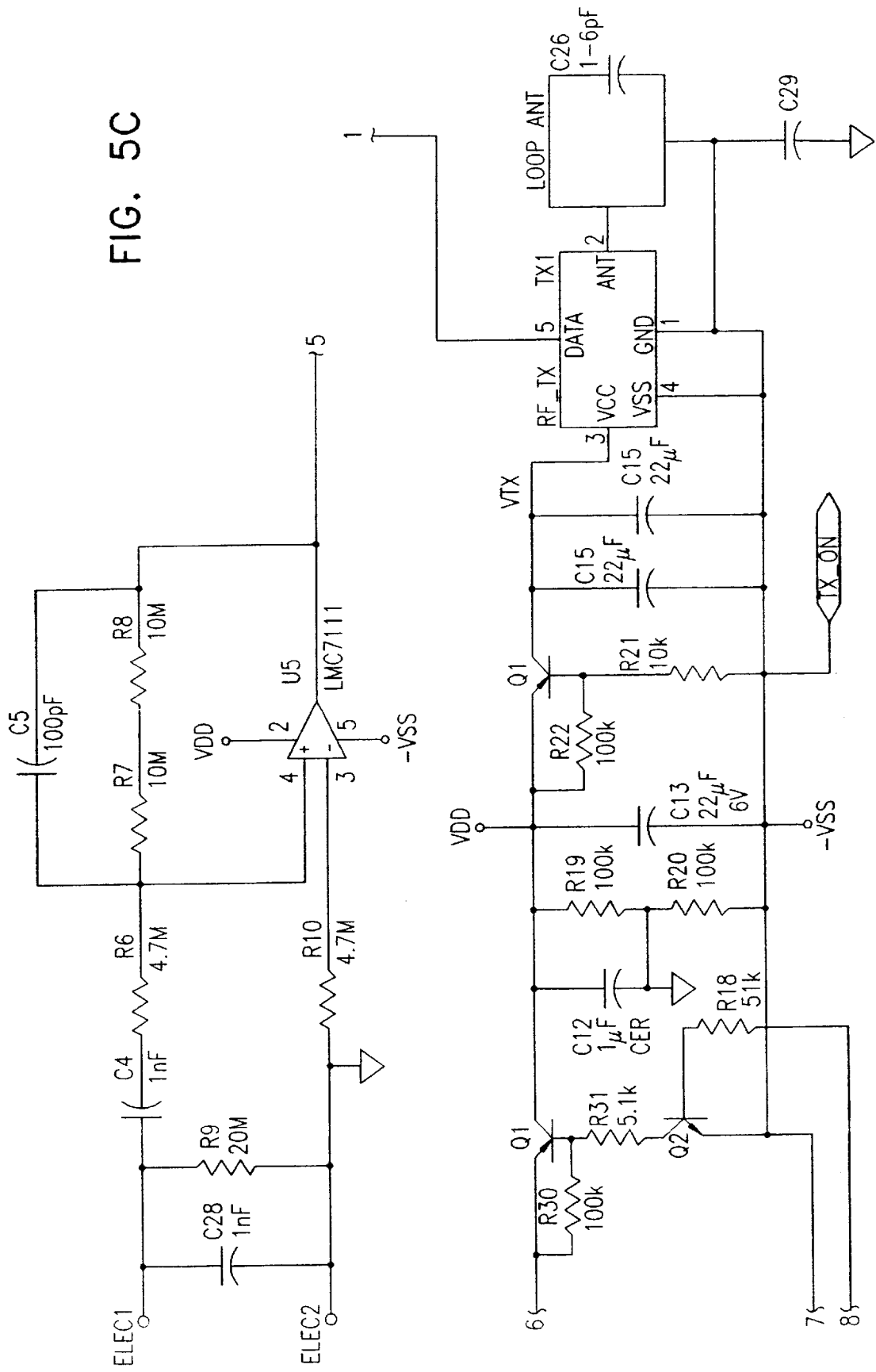
Figure 5D:
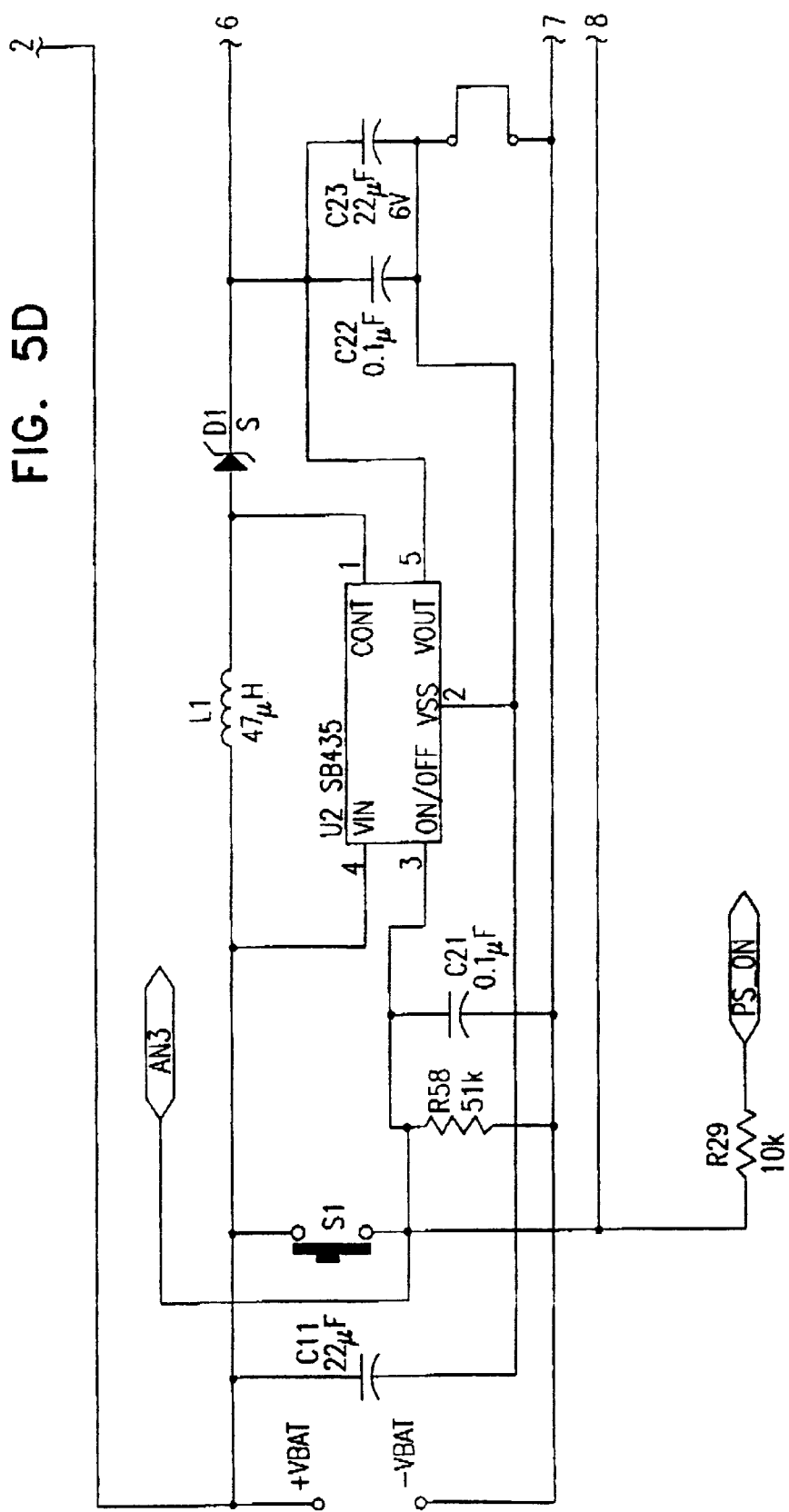
Figure 6:
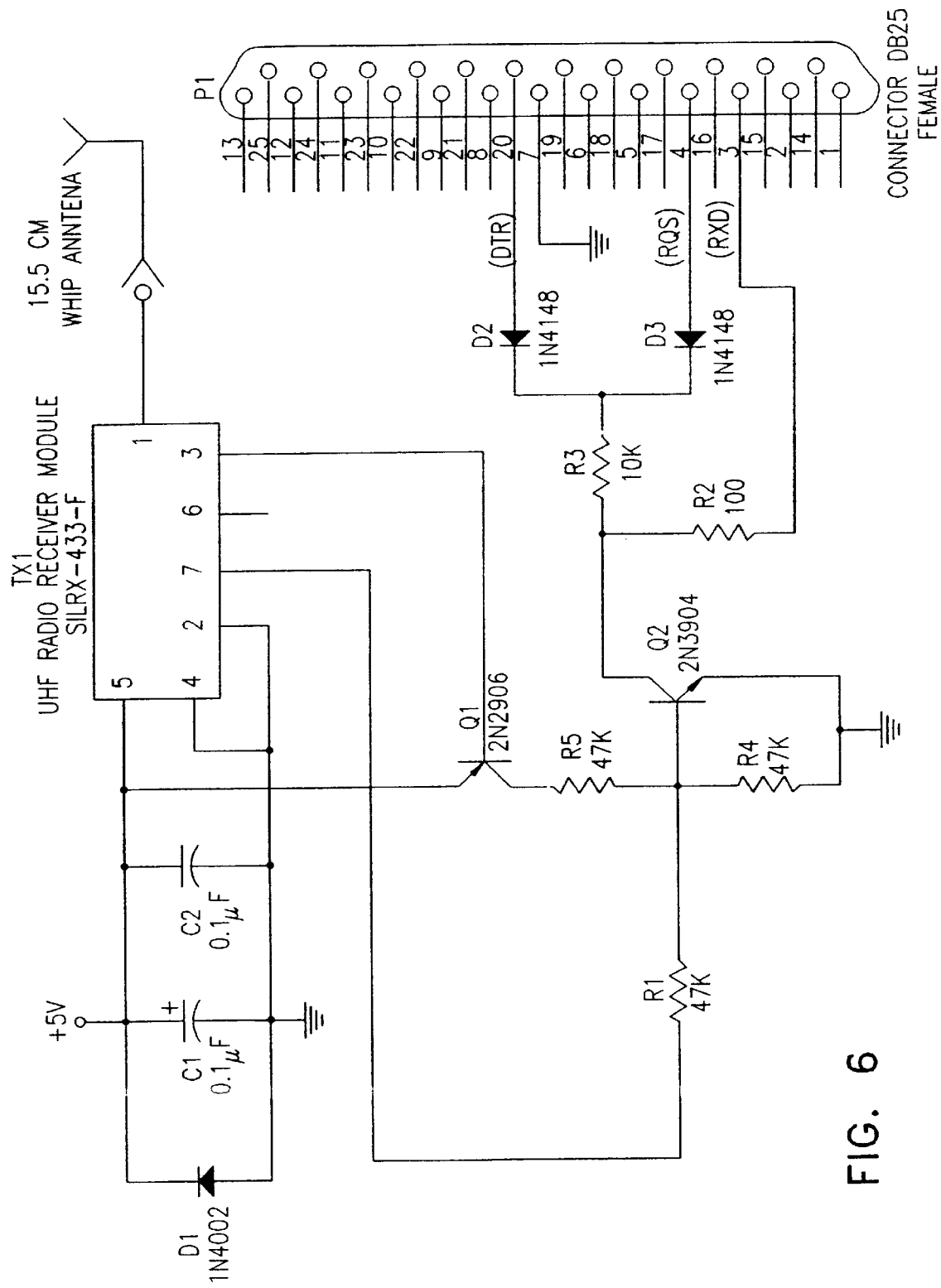
FIG. 6 is a schematic illustration of a wireless receiver employed in the circuitry of FIG. 3.

Reference is now made to FIG. 4, which is a simplified block diagram illustration of the electronic circuitry employed in the body mounted transducer assembly of FIG. 2. FIGS. 5A, 5B, 5C and 5D together provide a schematic illustration of the electronic circuitry of FIG. 4. FIG. 6 is a schematic illustration of a wireless receiver employed in the circuitry of FIG. 3. These figures are believed to be self-explanatory in view of the preceding description. Therefore, in the interest of conciseness, additional textual descriptions are not provided.

Figure 7:
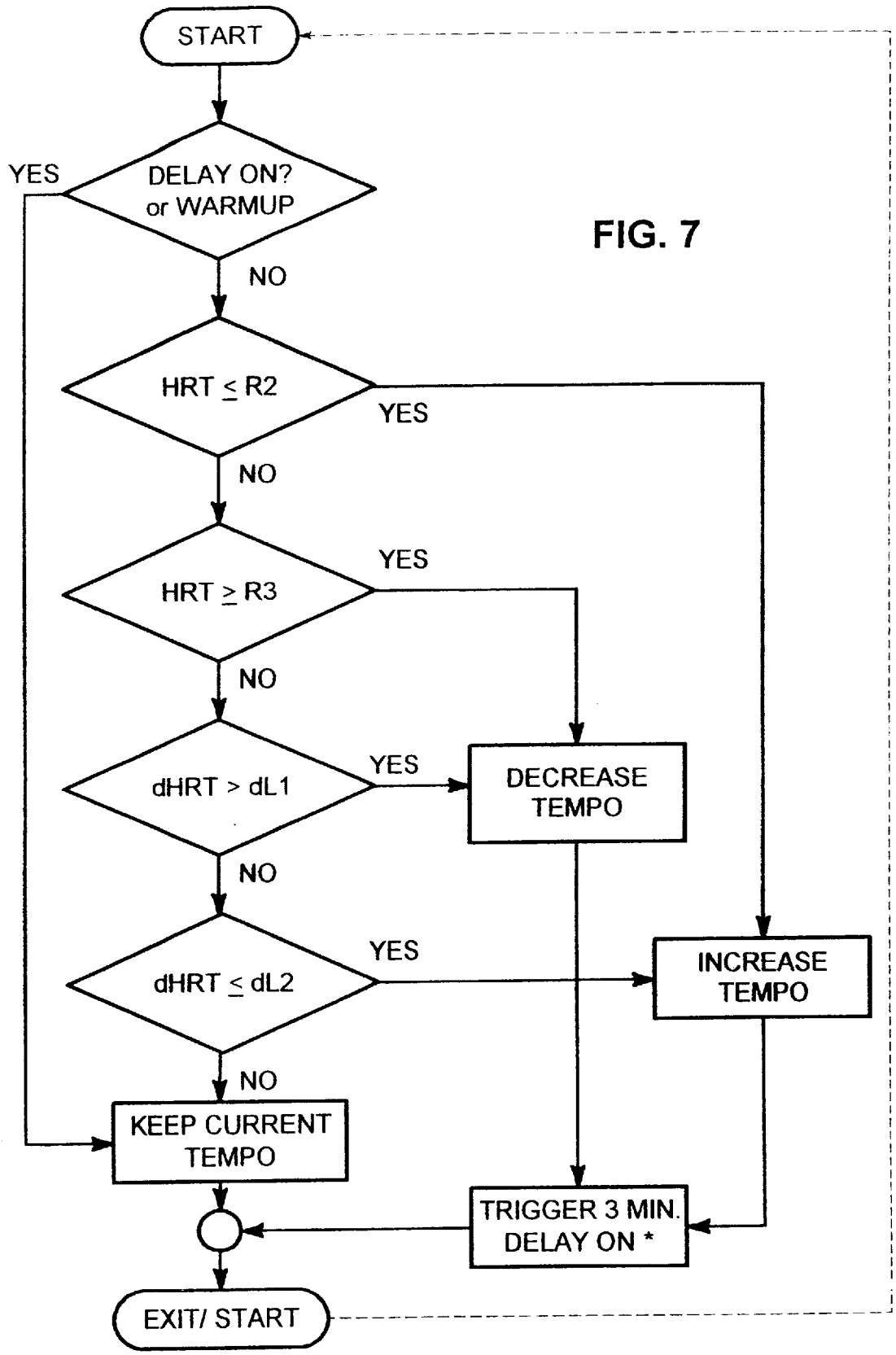
FIG. 7 is a simplified flow chart illustration of the operation of the system of FIG. 3.
Figure 8:
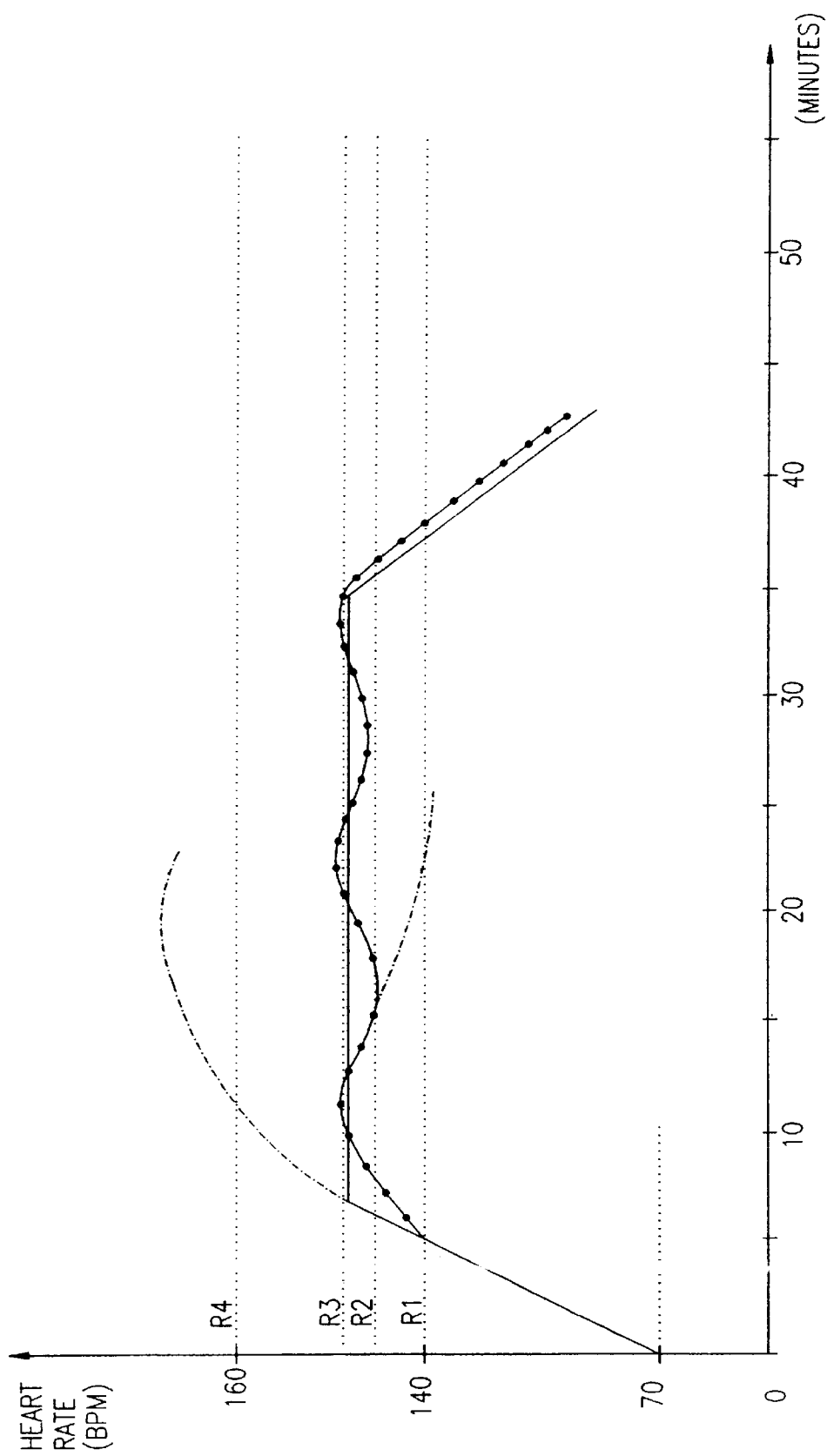
FIG. 8 is a simplified timing diagram illustrating operation of the system of FIGS. 3 and 7.

Reference is now made to FIGS. 7 and 8, which are respectively a simplified flow chart and timing diagram illustrations of the operation of the system of FIG. 3.

FIG. 8 illustrates the user's heart rate in beats per minute (BPM) in real time as a function of time from the onset of exercise. Indicated on FIG. 8 are respective minimum and maximum limits for user heart rate under aerobic exercise, R1 and R4 as well as preferred lower and upper limits for user heart rate during aerobic exercise, R2 and R3. The continuous line represents an ideal curve for the change in the heart rate as a function of time. The continuous-black-dotted curve represents a typical controlled fluctuation in the heart rate in accordance with a preferred embodiment of the present invention, as described hereinbelow.

A desired exercise motion parameter, such as the tempo of an audio output, is maintained constant during a warm-up period, which is defined as the concurrent occurrence of the following two conditions:

a. Within 3 minutes of the start of exercise; and b: User's heart rate is below R1, for example 140 BPM.

If the user's real time heart rate HRT is less than or equal to R2, the rate of the desired exercise motion parameter is increased, typically by increasing the tempo of the audio output. Once the tempo is increased, the tempo is maintained constant for a fixed period of time, preferably 3 minutes.

If the user's real time heart rate HRT is greater than or equal to R3, the rate of the desired exercise motion parameter is decreased, typically by decreasing the tempo of the audio output. Once the tempo is decreased, the tempo is maintained constant for a fixed period of time, preferably 3 minutes.

If the user's real time heart rate HRT is between R2 and R3 and if the time derivative of the user's real time heart rate HRT is greater than a predetermined maximum rate of change threshold dL1, the rate of the desired exercise motion parameter is decreased, typically by decreasing the tempo of the audio output. Once the tempo is decreased, the tempo is maintained constant for a fixed period of time, preferably 3 minutes.

If the user's real time heart rate HRT is between R2 and R3 and if the time derivative of the user's real time heart rate HRT is less than a predetermined minimum rate of change threshold dL2, the rate of the desired exercise motion parameter is increased, typically by increasing the tempo of the audio output. Once the tempo is increased, the tempo is maintained constant for a fixed period of time, preferably 3 minutes.

It may be appreciated that by using the present invention, a typical plot of a user's heart rate may appear to oscillate within the limits R2 and R3 as shown in FIG. 8.

It is appreciated that the circuitry of FIG. 3, as exemplified in FIGS. 7 and 8, samples the rate of change and direction of change of the heart rate, as well as the absolute value of the heart rate. If the above three parameters indicate that the user's heart rate will, unless changed, either exceed the upper desired heart rate limit or fall below the lower desired heart rate limit, the tempo of the exercise parameters supplied to the user, both visually and audibly are modified accordingly, so as to cause the rate of motion of the user to be modified such that the user's heart rate remains within the desired limits.

It is a particular feature of the present invention that in contrast to the prior art wherein corrective action is taken upon exceedance of the limits, the present invention avoids exceedance of the limits.

If no control is exercised over the heart rate, it is possible that the heart rate may rise above R4 or drop below R1.

Below are listed the instructions for installing the control program 62 and exercise program 64:

Minimum System Requirements

1. PC IBM® or compatible system with a Pentium® 100 Mhz processor;
2. 16 Mbyte Ram or more;
3. Audio card;
4. Video card with 1 MB RAM or more;
5. Hard disk with 100 Mbyte or more; and
6. CD-ROM driver X8.

Software Requirements

1. Windows® 95 environment;
2. Microsoft® Visual® C 4.2;
3. Delphi® Developer 2.0;
4. Microsoft® Visual Basic 4.0; and
5. ARJ (Version 2.41).

Installation Procedure

1. Load the condensed code on a file named:

"demo21.arj";

2. Recover the files:

"arjxdemo21";

3. Register the OCX files (using REGSRV32 delivered with Microsoft® Visual C 4.2);

4. EX.:

"regsvr32 exe21ocx.ocx"

"regsvr32 repmovie.ocx"; and

5. Run the "demo21.exe".

It will be appreciated by persons skilled in the art that the present invention is not limited by what has been particularly shown and described hereinabove. Rather the scope of the present invention is defined only by the claims which follow:

What is claimed is:

1. An interactive exercise monitoring method including:

(a) using a body mounted motion sensor to sense user motion during exorcise;

(b) sensing a user's heart rate; and (c) indicating to a user:

(i) an exercise motion parameter derived from an output of the body mounted motion sensor, and (ii) a desired exercise motion parameter for comparison therewith, said desired exercise motion parameter being derived from a comparison of a desired range of heart rate parameters with the direction and rate of change of the user's heart rate, wherein said indicating employs audible indications indicating the tempo at which user motion is to be carried out.

2. The method of claim 1, wherein said indicating further employs visual indications which indicate the motion that the user is supposed to carry out.

3. The method of claim 1, further comprising providing exercise pacing which senses whether the user is about to exceed desired upper or lower limits of heart rate and prophylactically changes the tempo, prior to exceedence of such limits, so as to urge the user to stay within the limits.

4. The method of claim 1, further comprising providing a visual indicator which indicates on a time scale both a desired pattern of movements and a user's actual pattern of movements, so as to enable and encourage the user to bring his movements into phase and tempo with the desired pattern.

5. The method of claim 1, wherein said heart rate and said user motion are sensed, respectively, by a body mounted heart rate sensor and motion sensor which are both incorporated in a single belt worn by the user during exercise, said belt including a wireless communication link.

* * * * *